United States Patent [19]

Krenmayr

[11] 4,021,122

[45] May 3, 1977

[54] GLASS CONTAINER INSPECTION MACHINE

[75] Inventor: Willy Krenmayr, Jona, Switzerland

[73] Assignee: Emhart Zurich S.A., Zurich, Switzerland

[22] Filed: July 1, 1974

[21] Appl. No.: 484,709

Related U.S. Application Data

[62] Division of Ser. No. 320,569, Jan. 2, 1973, Pat. No. 3,848,742.

[52] U.S. Cl. .................... 356/240; 209/111.7 T; 250/223 B; 356/198
[51] Int. Cl.$^2$ .................................. G01N 21/32
[58] Field of Search ......... 356/197, 198, 239, 240; 250/223 B; 209/111.7

[56] References Cited

UNITED STATES PATENTS

| | | | |
|---|---|---|---|
| 2,902,151 | 9/1959 | Miles et al. | 356/198 X |
| 3,089,594 | 5/1963 | Early | 250/223 B X |
| 3,245,533 | 4/1966 | Rottmann | 356/240 X |
| 3,262,561 | 7/1966 | Sorbie | 356/198 |

Primary Examiner—John K. Corbin
Assistant Examiner—F. L. Evans
Attorney, Agent, or Firm—McCormick, Paulding & Huber

[57] ABSTRACT

Containers are diverted from a conveyor onto a base where each container is rolled into an inspection station defined by three rollers. A side belt rolls the containers against a rail and one of the three rollers projects beyond the rail at said inspection station. The other two rollers are independently mounted on oscillating arms which move the side belts into contact with the container to rotate it at said inspection station. An improved inspection head is also disclosed, and the method of fabricating said head whereby the machine can be set-up for inspecting containers of various configuration with a minimum downtime of the machine, all of the light emitters and sensors being frozen in a block in a head for a particular container configuration.

2 Claims, 7 Drawing Figures

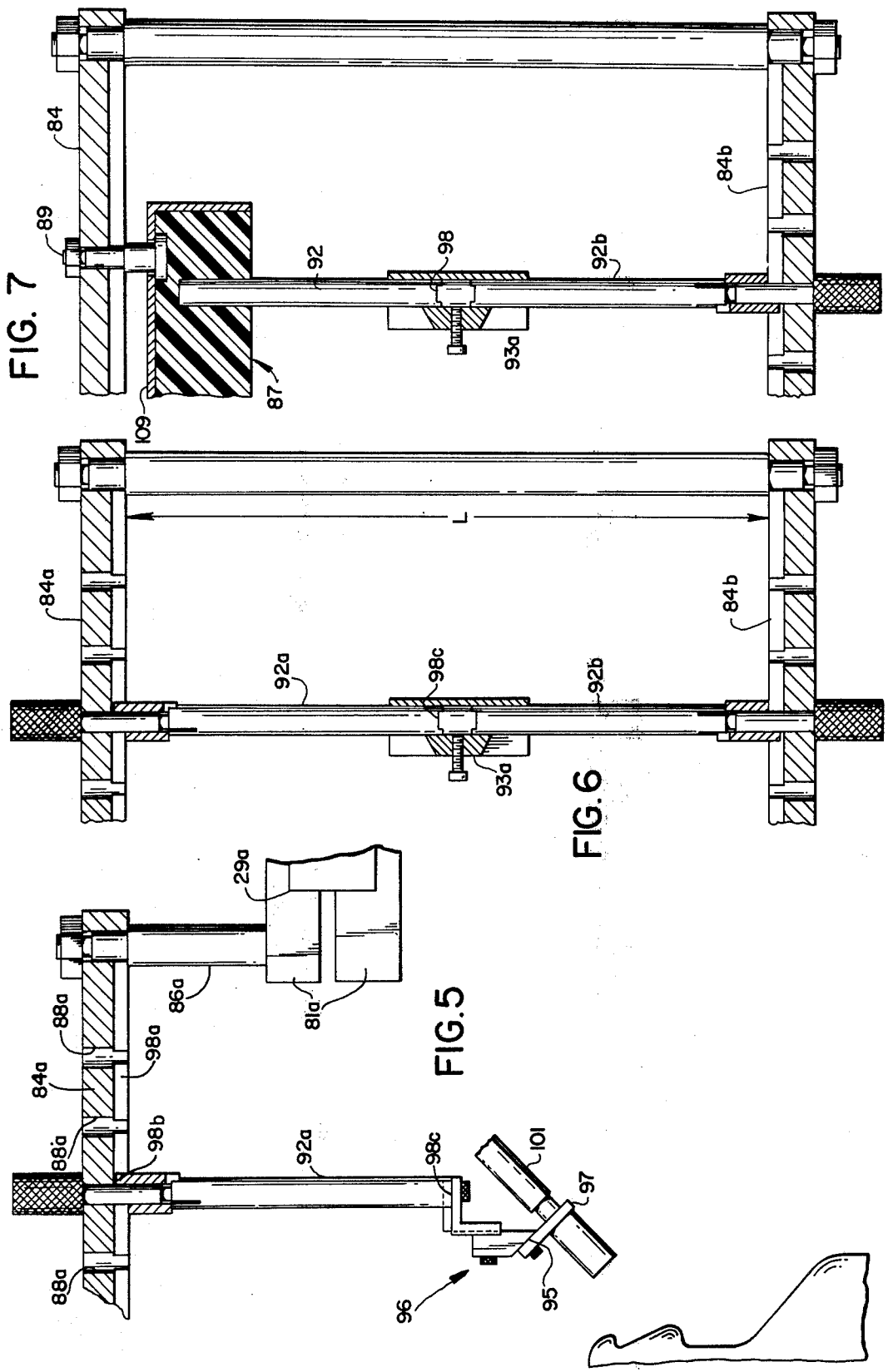

GLASS CONTAINER INSPECTION MACHINE

CROSS REFERENCE TO RELATED APPLICATION

This is a division of application Ser. No. 320,569, filed Jan. 2, 1973, and now issued as U.S. Pat. No. 3,848,742.

BACKGROUND OF INVENTION

Glass containers such as bottles, flasks or jars for the food industries or pharmaceutical industry, generally are produced in automated installations or plants. The production rates of such installations are very high. For example, containers with a unit weight of 100 g are produced at rates of up to 200 units per minute while containers with a unit weight of 900 g are produced at rates of up to 65 units per minute. To assure that contours or shapes, volumes (capacity) and other features of the containers are in accordance with product specifications including final use requirements, such as suitability for automatic bottling (filling and closing) which may require pressure sealing caps, crown corks or stoppers, a very rigid inspection of such critical features is required. Furthermore, the containers must be checked for absence of defects such as cracks, most importantly at the neck and bottom portion of the containers because such defects would increase the breakage hazard or render closing of the containers impossible. The term "crack", here, is intended to include various types of crizzles, splits, checks, fissures, blisters, spikes, jaggers and other defects inside the glass, whether they extend to a glass surface or not, capable of being spotted by deflection of light beams.

Both defects of contours or dimension and crack-type defects at the neck or bottom portions of the containers appear at random. Therefore, spot-checking or random-checking does not provide a sufficient quality control and each container produced must be examined individually. For this purpose, commercial container producing installations of the type mentioned above generally include inspection lines for checking the containers produced.

According to conventional practice, cracks at the neck or bottom portions of glass containers are detected by optical means. For example, in a typical crack-checking apparatus, each container is rotated around its vertical axis at least once, while at least one beam is directed at the article under inspection. For crack detection, the light emanating or being reflected from said container under predetermined angles is surveyed. This method works on the principle that cracks of the type mentioned above in vitreous substances are capable of forming an optical interface or boundary therein. Such a boundary will totally reflect a light beam with an angle of incidence greater than the critical or limiting angle of total reflection. This result is utilized to trigger a sensor for either accepting or rejecting that container.

In U.S. Pat. No. 3,533,704, issued in 1970 to the inventor herein, an inspection method is disclosed for taking advantage of this principle. Another approach is disclosed in U.S. Pat. No. 3,639,067 issued in 1972 to Stephens.

Most cracks are caused by stresses or tensions which result from initial cooling of the glass. While annealing may alleviate stresses it does not necessarily eliminate all cracks. The general direction of such cracks will usually be from the outer glass surface toward the inner surface of the glass container, that is predominantly in a radial direction. In order to detect substantially all such cracks regardless of their position and direction, a crack-checking apparatus generally includes several light emitters and several light sensors. Since the totally reflected light bundles have a width and, concomitantly an intesity, which increases as the angle of impact approaches the critical or limiting angle of total reflection, emission of the light bundle and the sensor or detector preferably are arranged such that the angle of the incident light approaches the limiting angle of total reflection. Further, in order to detect or sense totally reflected light, the incident light bundle and the light receiving part or sensor of the light detector should be in the same plane and be perpendicularly oriented with respect to the plane defined by the crack. It should be noted that the foregoing comments apply particularly to my prior U.S. Pat. No. 3,533,704 referred to above. Others have been successful in orienting light emitters and sensors in other ways for inspecting containers of various configurations. For example, the Stephens U.S. Pat. No. 3,639,067 illustrates a slightly different approach to the concept of inspecting glassware by optical means.

Whichever approach one chooses to follow, the technical problem is to arrange a plurality of light emitters or light sources, suitable for generating such light beams or bundles, and a plurality of coordinated light sensors or detectors under mutual angles which are functionally dependent upon the angles of reflection and refraction, and their positions will depend upon shape, contour and dimension of the containers to be tested. Mechanically, such an arrangement must be quite stable because the machines, and checking installations, are subjected to strong and continuous vibration, and also because it may happen in high speed production and its concurrent high conveying velocities that a container rebounds somewhere from the conveying line and hits the support of the testing devices or the testing devices proper. On the other hand, the arrangement or support should allow quick and reproducible setting or resetting of the testing devices so that upon a change of production from one size or type of container to another, readjustment is possible within a reasonably short time. The same testing apparatus can sometimes be used for continuously checking containers of various vertical heights when the neck or finish is similar to some other container configuration.

Inspection apparatus of various types are known and have, for example, been disclosed in U.S. Pat. No. 2,902,151 issued to Miles in 1959; No. 3,101,848 issued to Uhlig in 1963 and No. 3,249,224 also issued to Uhlig in 1063. These prior art machines do not show or suggest any standardized inspection head design, but instead generally include a number of vertical columns or rods interconnected by means of horizontal rails or cross bars with the optical testing devices mounted either on the rods or the rails by means of bars and pivotable brackets or knuckle joints. Such arrangements can be made to have sufficient mechanical stability but require frequent readjustment and, thus, repeated checking of the setting, because the original setting slowly changes under continuous vibration. Another important disadvantage of such prior art optical installations is that any new setting upon change of production requires highly skilled personnel and is quite time-consuming. For example, a new setting of a prior art checking apparatus typically may require up to ten hours while resetting of the production plant proper normally can be done within about an hour only. Thus, the time now required for a change of container production, be it in size or in type of the containers, will depend essentially upon the time required for setting the test components and, specifically, the crack-checking apparatus.

In order to obviate these problems it has been suggested to use a system of special support rods and pivotable clamps for mounting the test devices, the rods and clamps being provided with scales and circular divisions engraved thereon so that a setting once selected could be repeated or reproduced easily. Practice has shown, however, that such arrangements, while facilitating an approximative setting, still require additional fine setting which again is complicated and time consuming. Also, the engraved scales of the support rods and the circular divisions of the pivot clamps render such mounting devices quite expensive. U.S. Pat. No. 3,085,160 issued to Dahms in 1963 shows such a system. Modern automated plants generally produce glass containers of standardized shapes and dimensions and most commercial production machines have to be capable of producing a certain variety of such container types. Accordingly, it would be desirable to have a means for at least partially replacing prior art mounting and supporting mechanisms such as rods, rails, cross bars and clamps for supporting the testing installations with integrated arrangements in the form of testing heads for fixed or preset adjustment, each testing head being suitable for use in the inspection of a specific container type of a specific group of containers.

SUMMARY OF INVENTION

Accordingly, the invention relates to a crack-checking apparatus for the inspection line of an installation or plant for producing glass containers, said apparatus comprising conveying means to carry containers for testing in a distanced relation to a checking position where the vertical axis of said containers substantially coincides with a checking axis that serves as a reference axis, each container in said checking position being rotated at least once around its vertical axis. said conveying means further serving to carry said containers from said checking position to a transport installation, and said apparatus further comprising at least one optical checking arrangement including a light emitter for directing a light beam onto a predetermined area of a container in said checking position, and at least one light sensor cooperating with said light emitter to receive reflected light from said container, the apparatus being characterized by a testing head with fixed positioning rods for said optical checking arrangement, and by supporting means suitable for removably receiving and holding said testing head in a predetermined position relative to said checking axis.

Upon change of the production plant from production of one type of containers to another, the crack-checking apparatus according to the invention can be set within a couple of minutes and geneally setting or resetting of the crack-checking apparatus for a change of the type of containers produced can be effected within a time period shorter than that required for the change of the production plant proper. An additional advantage is that such setting or resetting of the crack-checking apparatus can be done by unskilled or semi-skiller personnel and without subsequent control of containers produced during the period of transition from one container type to the other. According to the art, the containers produced during the period of transition cannot be inspected automatically and require post-checking. As the invention provides for complete reproducibility of a given setting of the the testing devices, the quality of testing can be improved. Also the integral and substantially unchangeable mounting of the testing devices will not be changed by strong vibrations of the plant even during extended operational runs.

BRIEF DESCRIPTION OF THE DRAWINGS

An embodiment of the invention will now be explained with reference to the drawings in which:

FIG. 5 is an elevational view of a bench set-up or jig for use in practicing the method of fabricating an inspection head according to my invention.

FIG. 6 is another elevational view (partly in section) of the jig of FIG. 5.

FIG. 7 is still another elevational view of additional apparatus for fabricating an inspection head according to my invention.

DETAILED DESCRIPTION

Figure 1:
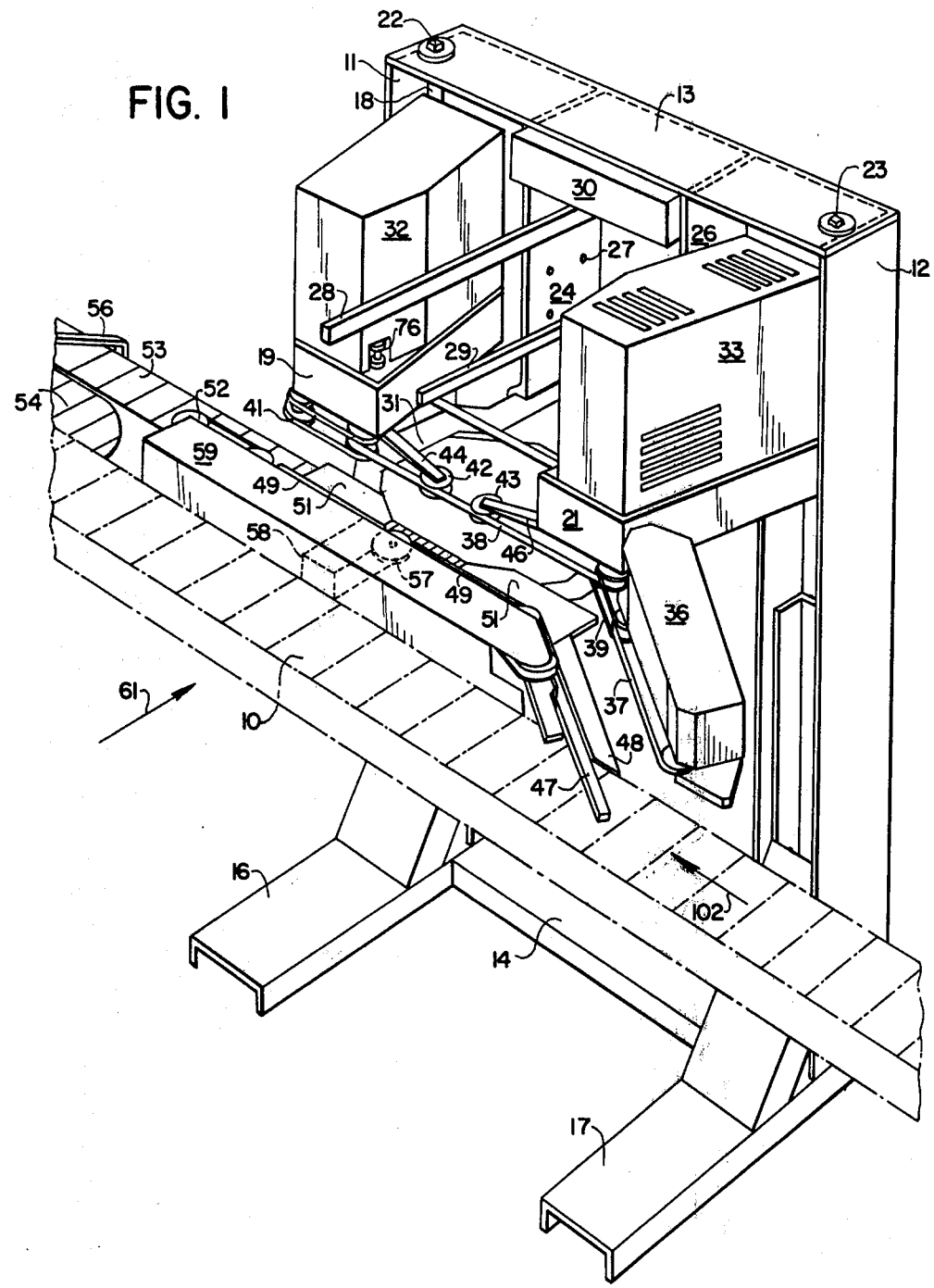
FIG. 1 is a simplified prespective view of an embodiment of the crack-checking apparatus according to the invention but with the inspection head omitted for clarity.

The arrangement of FIG. 1 includes a main conveyor 10, made, for example, of plates or the like interconnected to form an endless belt arrangement, of a conveying installation for transporting the containers to the various stations of an inspection line. The particular station shown in FIg. 1 is a crack-checking apparatus arranged alongside the conveyor 10 and comprising means for carrying the containers in spaced relationship to a station where each container is rotated momentarily and then returned to the conveyor 10, or rejected. A testing head, and electronic measuring and computing installations are all supported by a frame or chassis arrangement.

The frame includes two vertical support structures or beams 11, 12 each having a U-shaped cross-section and both being connected by horizontal beams 13 and 14, the connections normally being welds. For increased stability of the frame, the lower ends of the support beams are provided or connected with horizontal base plates 16, 17. The open ends of U-shaped beams 11, 12 extend towards conveyor 10. Arranged within beams 11, 12 are vertical helices or spindles 18 (only one spindle being visible in FIG. 1) carrying gear boxes 19, 21 which constitute parts of the conveying means. Both spindles extend through vertical beam 13 and are guided by spindle heads 22, 23. The two adjacent side walls 24, 26 of U-shaped beams 11, 12 include several borings 27 arranged in pairs of vertical series and serving to support and secure a pair of arms 28, 29 in several different levels above the main conveyor. A frame portion 31 further connects the adjacent sidewalls 24, 26 of the beams. Arms 28, 29 serve as supporting means for a testing head (to be described more in detail below), while frame portion 31 serves to support further machine units (also to be described more in detail below). At both ends of beam walls 24, 26 and below beam 13 a housing 30 is mounted to receive electrical and electronic measuring and testing devices which cooperate with the testing head. Arranged above each gear box 19, 21 is a driving motor (not shown in FIG. 1) with coordinated switching devices and covered by lids 32, 33. Gear box 21 on the entry side of the apparatus supports a feed-in arm 36. This arm extends towards main conveyor 10 and carries a feed-in friction band or belt 37 which is guided by a set of rollers. Downstream, a central friction band or transport belt 38 is provided, also guided by a set of rollers mounted below gear boxes 21, 19. The transport belt has a generally linear active run extending between an upstream pulley 38$a$ in the box 21 and a downstream pulley 38$b$ in box 19.

Figure 3:
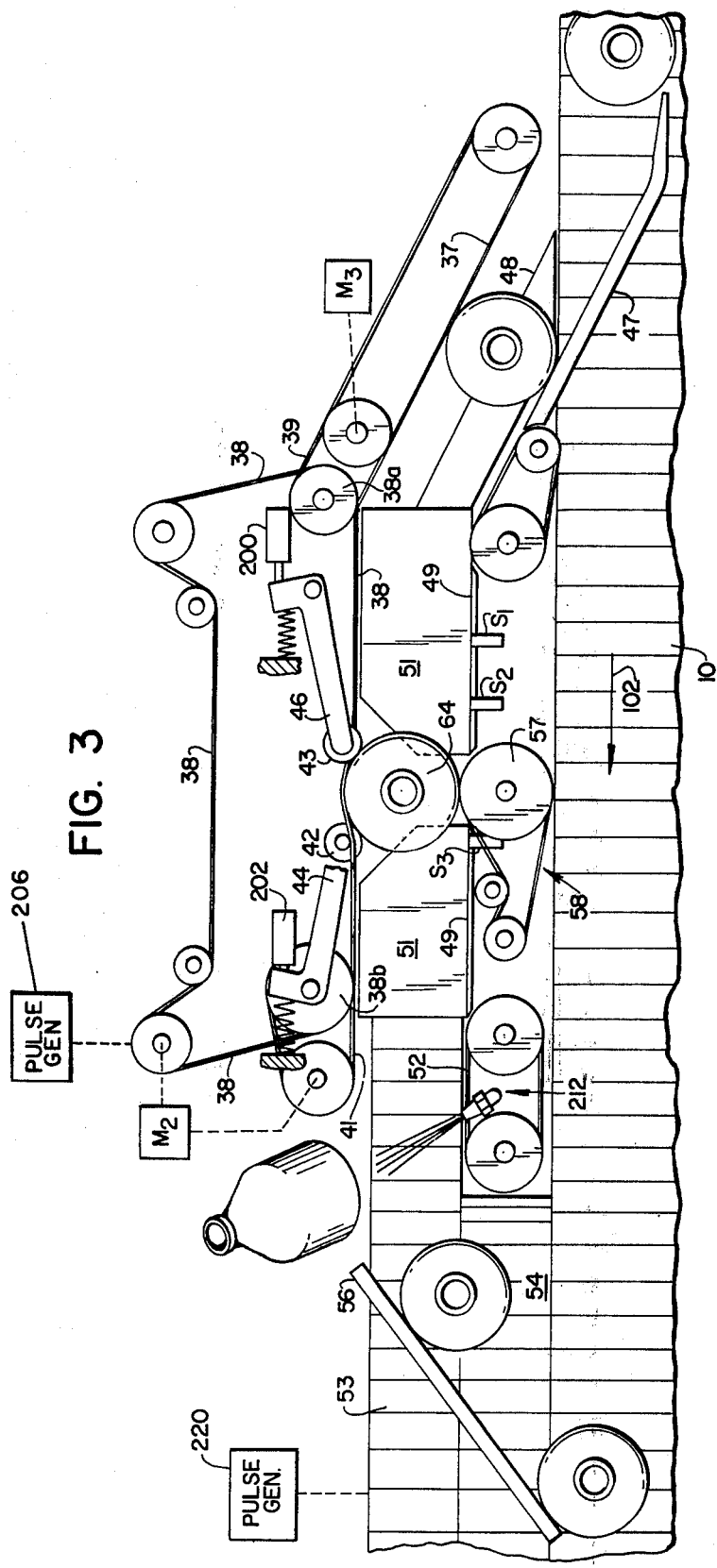
FIG. 3 is a schematic plan view of the container handling portion of the apparatus shown in FIG. 1, including the transport belt.

A double-action transfer friction belt 39 is arranged between feed-in friction belt 37 and transport belt 38, while a first double-action brake friction belt 41 is arranged downstream of the said active run of the transport belt. The transport belt cooperates with two pressure rollers 42, 43 mounted on pivot arms 44, 46 respectively. These arms are capable of pivoting independently of one another in a horizontal plane as described more in detail below. The various friction belts or bands are not only guided by the rollers shown in FIG. 1 but additional rollers shown in FIG. 3 of the drawings are also arranged to return, tension and drive the belts. Referring more particularly to FIG. 3, the transport belt 38 is preferably driven continuously by a motor $M_2$, and this belt is also entrained on additional pulleys also located in the main frame of the machine. Another motor $M_3$ drives the friction belts 37 and 39. The belt 41 at the exit end of the main frame is driven by the motor $M_2$, but in a direction opposite that of the other belts 37, 39 and 38. Still with reference to FIG. 3 and to the main frame of the machine, the pressure rollers 42 and 43, and more particularly the respective axles or stub shafts upon which they are mounted, serve to wrap a segment of the belt 38 around a portion of the periphery of the container being inspected. The downstream or second arm 44 is spring biased toward the active position for so wrapping the belt 38. The upstream, or first arm is spring biased toward its inactive position and a solenoid device 200 is selectively operable as suggested in FIg. 4 to move the arm 46 into its active position.

Having thus described that portion of the main frame of the machine relating to the container handling means, the complementary unit of the conveying means will now be described. The complementary machine unit of the conveying means is adjustably connected with frame portion 31 to accommodate articles of various diameter. This unit is arranged substantially at the level of the above described friction belts. It includes an entry or feed-in guide rail 47 on the entry side and in juxtaposition to arm 36, a bottom guide plate 48 and, in the area of the central friction belt, a central rail 49 consisting of upstream and downstream portions, and a central bottom plate 51 composed of several platelets. This unit further includes a second brake friction belt 52 on the exit side and juxtaposed to brake friction belt 41. Adjacent to central bottom plate 51 is a two-partite outfeed transfer belt arrangement 53, 54 actuated by a motor (not shown). Guide rail 56 is provided above the outfeed transfer devices such that the component belts and the guide rail are capable of conveying the tested containers back onto main conveyor belt 10. A central or back-up wheel 57 is arranged between the two components or portions of central guide rail 49. Preferably, this wheel is under spring tension and connected with a drive and brake arrangement 58. The back-up wheel 57 has an active segment which extends beyond the rail 49 and as so oriented said wheel cooperates with the idler rollers 42 and 43 to define the inspection station therebetween. The back-up wheel drive and brake unit 58 is operated by control means to be described in greater detail with reference to FIG. 4. Both parts of the central guide rail as well as the guiding roller and the second friction band are covered in part by lid 59.

Figure 2:
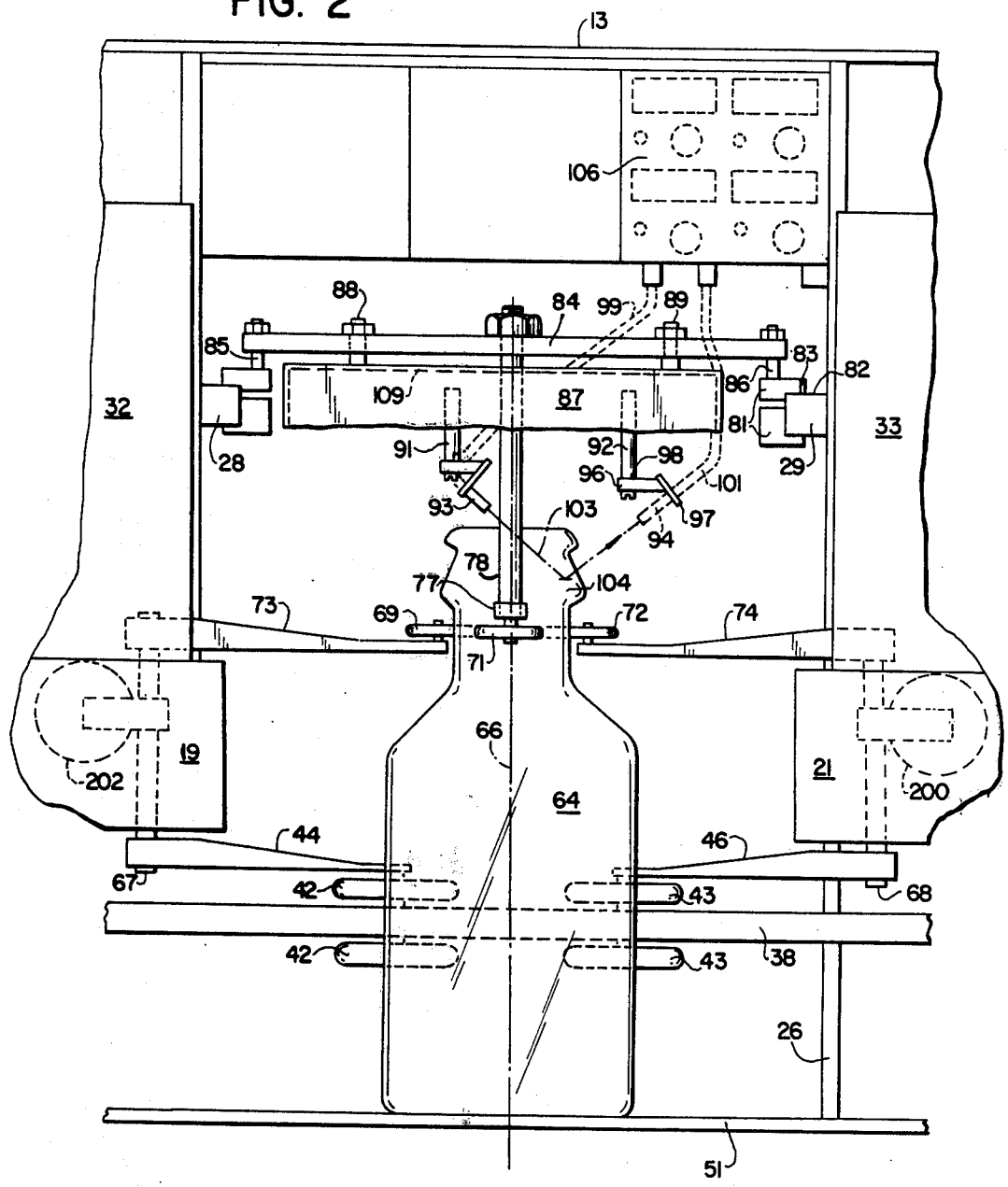
FIG. 2 is a side view of the central part of the apparatus of FIG. 1, showing the inspection head in elevation.

FIG. 2 shows a side elevational view of the central portion or inspection station of the crack-checking apparatus, as viewed in the direction of arrow 61 in FIG. 1, the portions of the complementary machine unit being omitted from this view for clarity. A container 64 is supported by central bottom plate 51 and is guided by pressure rollers 42, 43 and by the back-up wheel 57 such that its vertical axis substantially coincides with a fixed testing reference axis 66, the latter being determined by the set-up of the checking apparatus. The container is rotated around the checking axis by means of friction belt 38 substantially at the level of the containers' center of gravity. As is apparent from FIG. 2, arms 44, 46 supporting pressure rollers 42, 43 are mounted on rock shafts 67, 68 which protrude from gear boxes 19, 21. For guiding the container in the area of the container neck, a further guiding arrangement is provided. This includes three rollers 69, 71 and 72. Rollers 69, 72 are supported by pivotable arms or levers 73, 74. The levers are supported on the upper ends of the rock shafts 67, 68 which protrude from gear boxes 19, 21. The upper end 76 of shaft 67 is shown at the top of gear box 19 in FIG. 1. The third roller 71 is supported by an intermediate member 77 pivotally mounted on a support rod 78 and capable of being pivoted radially to the testing axis, i.e. vertically to the plane of the drawing.

Each arm 28, 29 supports at least one two-partite clamping member 79, 81 which may be tightened securely onto the corresponding arm, e.g. by screws not shown. One arm 29 is provided with a marker 82 while the coordinated part of clamp 81 comprises an indicator 83. With the help of such marking means the clamp can be repeatedly secured at a predetermined location by shifting in the longitudinal direction of the arm, i.e. vertically to the plane of the drawing. At the upper part of the clamp a support plate 84 is mounted and secured, and the distance between clamp and plate can be adjusted by means of replaceable shim jackets or tubes 85, 86. Support plate 84 comprises at least two, and preferably four borings, which are accurately located with respect to axis 66. A mounting block 87, made for example by molding and setting of duroplastic resin, is arranged below the support plate. Support bolts 88, 89 are located in the boring of plate 84 and are embedded in the block. Several support or mounting rods are embedded in the mounting block. Rod 78 supports the third roller 71 of the guiding installation. The two other rods 91, 92 of the embodiment shown are provided to carry a light emitter 93 and a light sensor 94. A system or pair consisting of a light emitter and a light sensor will be understood to constitute an optical checking unit. In the embodiment shown, the light emitter and the light sensor are not directly secured to the support rod. In order to arrange either light emitters or light sensors on any rod at various distances and in various angular positions, the free end of each rod is provided with a support 96 having a tapered end portion 95 provided with a securing plate 97. Support rods 91, 92 and exchangeable carriers are provided with a groove-and-tongue joint arrangement 98 so that the orientation of the support rods are precisely defined in a horizontal plane, vertical to the plane of FIG. 2 of the drawings. The light emitter and light sensor are well known optical systems. In the embodiment shown, the light emitter receives light from a remote light source by means of a glass fibre bundle 99. The light sensor also is connected with a glass fibre bundle 101 to carry any light received by the sensor to a light-sensitive element, generally referred to as a light detector.

When the testing apparatus is in operation, containers on the main conveyor 10 will be conveyed in the direction of arrow 102 (FIG. 1) and interupted by entry guide rail 47, and will come in contact with friction belt 37. The distance between the entry guide rail and the juxtaposed friction belt corresponds substantially with the diameter of the container tested so that the containers, one after the other, are received by the friction belt and rolled on bottom plate 48 in upright position and along entry guide rail 47. The belt is driven at such a speed that the containers are advanced or rolled on plate 48 at a somewhat slower speed than on the main conveyor 10. Transfer belt 39 operates substantially at the same speed as the entry friction belt 37 so that the containers are rolled at constant speed and in close sequence onto central bottom plate 51. Central friction belt 38 operates at a speed greater than the entry friction belt. Therefore, the containers are rolled more speedily along the central guide rail 49 than along the entry guide rail 47 and therefore the container spacing is caused to increase between the individual containers on the base 51. Prior to entry of a container into the inspection station, pressure roller 43 on arm 46 will be pivoted out of the path of the container, in the direction toward the main frame of the machine so that the container will abut the downstream idler or roller 42.

Figure 4:
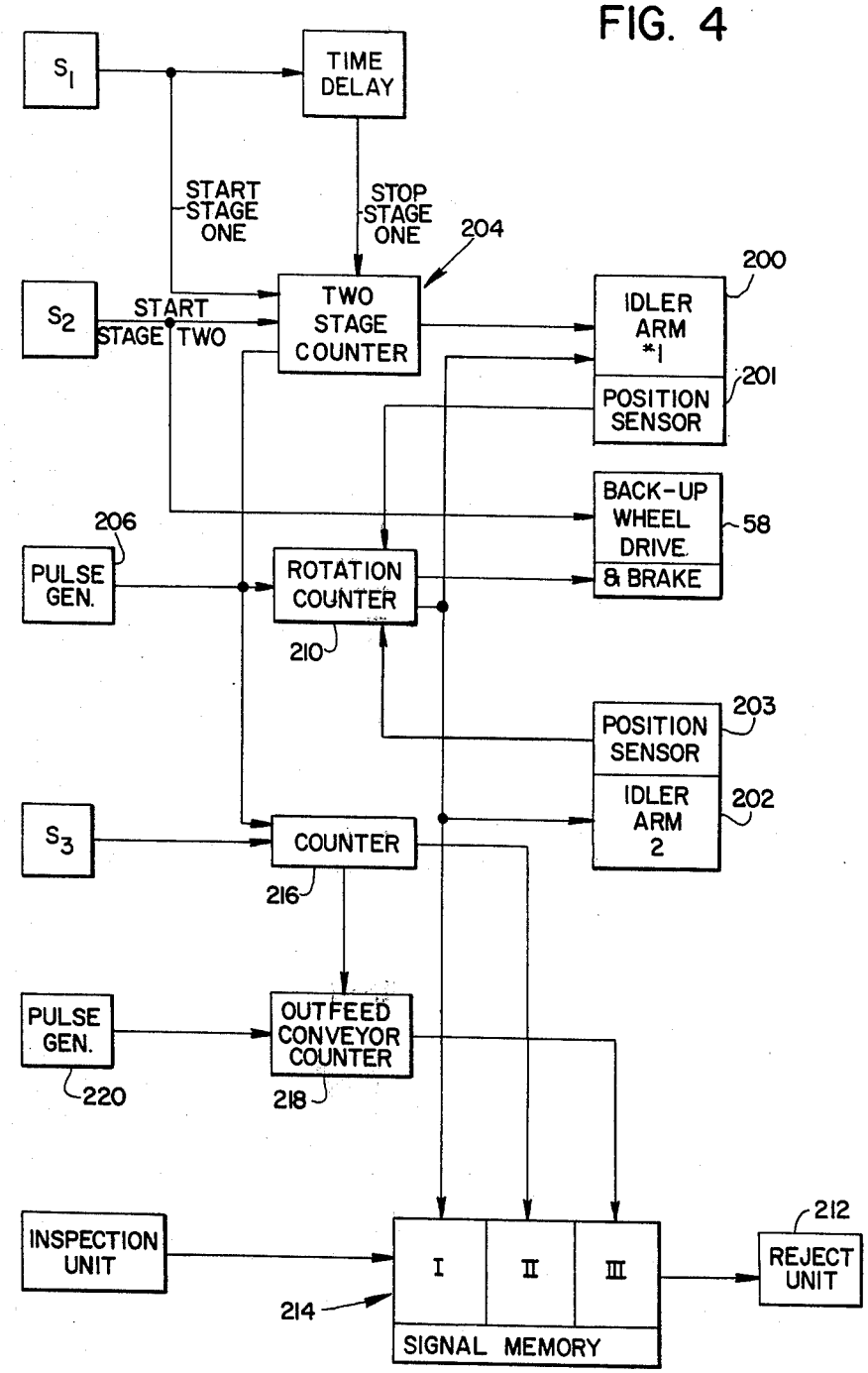
FIG. 4 is a schematic block diagram showing the mode of operation for the various components depicted in FIG. 3

Referring now to FIGS. 3 and 4, a series of proximity switches $S_1$, $S_2$ and $S_3$ are provided in the path of each container on the base 51 as it is moved by the belt 38 into the inspection station, and after it is released therefrom. Closing of switch $S_1$ starts a brief time delay and triggers a counter 204, which counter receives a clock pulse timed to the conveyor 10, through a pulse generator 206. As the next switch $S_2$ closes, counter 204 provides an input to the solenoid operator 200 for the upstream or first idler arm causing roller 43 to move into its active position, and thus trapping the container 64 at the inspection station. Switch $S_2$ also activates the back-up wheel drive portion of unit 58. This unit is designed to drive the wheel 57 up to a speed of approximately 80% of the design angular rotation for the particular container to be spun, and then to declutch this drive, all upon closing of $S_2$.

A position sensor 201, associated with the first or upstream idler arm 46, provides a start pulse to rotation counter 210, which counter is also clocked through the main conveyor pulse generator 206. Upon expiration of a predetermined count set in counter 210 (corresponding to at least one complete revolution) an input is provided to the back-up wheel brake portion of unit 58, and to the control unit 202 associated with the second or downstream idler arm 44. Thus, the inspected container is decelerated on the side opposite the transport belt 33, and roller 42 swings clear of its path allowing the container to be rolled out of the inspection station.

As explained above, back-up wheel 57 is driven during entry of a container into the inspection station, the direction of rotation being opposite to the direction of operation of transport belt 38. The peripheral speed of the central roller corresponds to about 80% of the speed of movement of the central friction belt. As soon as the container rolling along the first part of central guide rail 49 comes in contact with central roller 57 rotating in an opposite direction, the movement of the container through the transport installation, i. e. the movement of translation, will be braked and stopped. In order to prevent rebounding of the container, the entry pressure roller 43 will be pivoted back into the operating position shown in FIG. 3 so that the container will be guided by pressure rollers 42, 43 as well as central roller 57 and rotated in place, i. e. there is no movement of translation. It will be understood that rollers 69, 72 which contact the container neck will be pivoted simultaneously in the same direction as pressure rollers 42, 43.

While the container is rotated at the inspection station, the areas of the containers to be checked or inspected for defects or cracks of the type explained above, particularly for detecting such defects in the area of the container outlet and the lower neck or shoulderportion, will be impinged by light from several light emitters 93. When a light bundle 103 impinges upon a crack 104, light will be reflected, and the reflected light bundle will impinge upon a light sensor 94. In order to exclude noise signals as far as possible, both the light emitter and the light sensor are provided with an optical lens system so that the emitted or reflected light bundle will have a small diameter, and that the light sensor will receive light bundles of a well defined direction. Since each light emitter and corresponding light sensor will be capable of checking a limited portion or area of the container only, a plurality of light emitters and light sensors will be required. In technical operation of a commercial apparatus up to twelve light emitters and up to twenty light sensors will be used. In order to arrange such a large number of light emitters and light sensors in the available space (for example, they must not be in the path of the containers nor hinder their movement), The light sources as well as the light detectors or multipliers are arranged in a position remote from the checking position, e. g. within electronic control box 106. Conduction of light from control box to emitter and from the light sensor to the control box again can be effected by means of light conductors 99, 101. While a single optical checking arrangement (i. e. a pair of one light emitter and one light sensor) and a single control box is shown in FIG. 2 only, it is to be understood that several checking installations as well as several control boxes will be required for commercial operation.

Each light bundle reflected by a crack will trigger a control signal to operate a mechanism of rejection 212 so as to eject a defective container after such container has left the inspection station. As shown in FIG. 3 the reject device 212 is preferably an air operated device capable of removing the defective container by blowing it off the first of two outfeed conveyors 53 at the general location shown. The inspection equipment described above will provide a reject signal to a signal memory device 214, which device has three stages to delay operation of the reject unit 212 until the defective container reaches the position for rejection. The first stage assures that the container is fully inspected, the second stage assures that the container has left the inspection station and had time to move to the end of the belt 38. Finally the third stage is associated with a counter 218, which counter 218 is started by the output from the same counter 216 which satisfies stage II of signal memory 214, but which counter 218 is clocked by a pulse generator 220 associated with the outfeed conveyor 53. When all three stages of signal memory 214 have been satisfied reject unit 212 is energized, removing the defective container from outfeed conveyor 53.

As soon as the container has completed at least one full rotation around its axis, exit pressure roller 42 supported by arm 44 will be pivoted out of the path of movement of the container and towards the chassis frame, While central roller 57 will be stopped simultaneously. As soon as the peripheral velocity of the central roller will be slower than the speed of movement of central friction belt 38, the container will be moved along the roller and transported out of the inspection station. It will then roll along the exit part of central guide rail 49. At the end of both the central rail and the central bottom plate the container will be received by brake friction belts 51, 52 rotating in opposite directions so that the rotation of the container will be braked and the container with no rotational movement will be moved onto outfeed conveyor 53 arranged at the end of the conveying installation.

By way of summary, the pivoting movement of the pressure rollers 42 and 43 will be controlled by switches $S_1$ and $S_2$. These switches are arranged in the entry part, and another $S_3$ in the exit part. Acceleration and braking of the back-up wheel will be effected electrically, and will depend upon the pivoting movement of the pressure rollers.

In a test set-up which would be typical of commercial installation, the crack-checking apparatus according to the invention was found capable of testing 250 containers per minute, each container having a diameter of 70 mm and a weight of about 250 g. The residence time of a container at the inspection station, (i. e. the time period required for checking) was only about 0.1 seconds.

In order to adapt the crack-checking apparatus for processing containers of different dimensions, the main frame of the machine including the gear boxes with attached pressure rollers as well as the rollers of the guiding installation and the friction belts, can be displaced in vertical and horizontal directions.

For adjusting a testing head of the type disclosed in FIG. 2 a set-up fixture, best shown in FIGS. 5, 6, and 7, will be described. A support plate 84a, corresponding to plate 84 in FIG. 2, will first be arranged in the checking apparatus or in a simulating device or set-up fixture. This horizontal plate 84a includes a plurality of vertical borings 88a, 88a, which are preferably arranged in line with keyways or grooves 98a, 98a. That is, each boring 88a is provided with a keyway or groove which will receive a tongue portion 98b on each of the auxiliary support rods 91a, and 92a. The actual number of such auxiliary support rods corresponding to the number of the optical checking installations and all of said rods are secured in borings 88a, 88a of the support plate 84a. These auxiliary support rods 91a and 92a are provided at those ends which are to be inserted into the borings with tongue portions 98b capable of being inserted into the groove portions 98a thereby preserving a desired orientation of the rods. The auxiliary support rods 91a and 92a can be of different lengths so as to provide for securing of the optical checking installations at different distances from the support plate 51, or from the containers to be checked. At the lower, or free end portion of each auxiliary support rod 92a a carrier 96 is secured having a laterally displaced tapered free end 95. In order to mount and secure light emitters and light sensors in different distances and with different inclination vis-a-vis the container to be checked, carriers of different length and of different taper can be used. Furthermore, the lower end of each auxiliary support rod also comprises a groove portion 98c while the coordinated face of each carrier comprises a mating tongue portion as shown in FIG. 5. To set the optical checking installation in different alignments, carriers having tongue portions in differing arrangements can be used. When the light emitters and light sensors are optimally adjusted by means of a test-container set in checking position, a data sheet defining the carriers used as well as their coordination with the auxiliary rods will be prepared. Thereafter, the carriers may be dismounted from the auxiliary support rods. The support plate 84a with the auxiliary support rods then are secured in the set-up of FIG. 6. Guiding rods 91b and 92b are inserted in exact justaposition to the auxiliary support rods 91a and 92a in an auxiliary support plate 84b. The guiding rods will be connected to the free ends of the auxiliary support rods by unions 93a, 93 a. Each union and rod end have mating tongue and groove portions similar to the ends 98b of the auxiliary support rods. The lower, or auxiliary support plate 84b, with its coordinated guiding rods 91b and 92b then constitutes a "negative" or a stencil for the upper plate 84a with the auxiliary support rods 91a and 92a. Upon separation of the upper support plate 84a, with the auxiliary support rods 91a and 92a from the auxiliary support plate 84b with the guiding rods 91b and 92b, the free ends of the guiding rods can be provided with the support rods 91 and 92. The groove end portions of these support rods shown in FIG. 7 mate with the tongue portions of the guiding rods, and the lengths of each support rod is such that its length, when combined with its guiding rod provides a constant length L in FIG. 6. This arrangement of each support rod, such as 92, will then be mounted in a casting mold, which mold is filled, subsequently, with a molding or casting composition, preferably a duroplastic resin composition, comprising an epoxy resin. After setting or solidification of the casting composition and dismounting of the guiding rods from the support rods, the testing head 87 thus produced can be inserted into the crack-checking apparatus, or inspection machine of FIG. 1.

Now, according to the embodiment illustrated in FIG. 1 and explained previously, a testing head which includes a mounting block and support rods can be used, after reassembling the carriers per the data sheet, to check containers of differing dimensions or shapes. It is possible, therefore, to permanently secure the carriers on the support rods and to use a separate testing head for each type of container. Also, it is not required to fix the optical testing installations in the manner described above and different means of securing light emitters and light sensors can be used, such as securing them in a boring at the lower end of the support rods. The set-up fixture used for the preparation of the mounting block can be used repeatedly.

Further, it is possible to leave the mounting block in the mold so that the mold 109 (FIG. 2) forms a part of the testing head. When the mounting block is removed from the mold after setting or solidification of the casting composition, the support bolts must be embedded in the block. When the casting mold 109 is used as a part of the testing head 87, the support bolts can be secured in the casting mold. By selecting borings 27 (FIG. 1) for securing of arms 28, 29 and selecting the length or height of the intermediary shim jackets, or tubes 85, 86, the testing head, for example, can be secured in any required level above central bottom plate 51 for checking of containers of different height.

I claim:

1. In a glass container inspection machine of the type having an inspection station and means for rotating each container on a fixed base and on a fixed reference axis at such station the improvement comprising:
   a. an inspection head for a plurality of light emitter and sensor means for said inspection station;
   b. means for supporting said light emitters and sensors in said inspection head, said supporting means including;
   c. a molded block of plastic material supported at a predetermined height above said base;
   d. a plurality of rods having their upper ends embedded in said block in a predetermined pattern, and having the lower ends thereof located at various predetermined distances above said base;
   e. a plurality of horizontally extending support members carried by the lower ends of said rods respectively and
   f. each of said support members oriented at a predetermined angle in its horizontal plane,
   g. said light emitters and sensors being carried by said support members in spaced relation to said rods and at predetermined angles with respect to said rods.

2. The combination defined in claim 1 wherein said block comprises an epoxy resin of heat and age resistant composition, and a plurality of inspection heads for use in said machine, all of said heads having epoxy blocks and rods arranged in particular patterns to support corresponding members and light sensors and emitters for inspecting a variety of styles and sizes of glass containers.

* * * * *

UNITED STATES PATENT OFFICE
CERTIFICATE OF CORRECTION

Patent No. 4,021,122         Dated May 3, 1977

Inventor(s) Willy Krenmayr

It is certified that error appears in the above-identified patent and that said Letters Patent are hereby corrected as shown below:

Col. 2, line 53, "1063" should be --1963--.

Col. 3, line 44, "axis." should be --axis,--.

Col. 3, line 61, "geneally" should be --generally--.

Col. 4, line 43, "FIg." should be --FIG.--.

Col. 5, line 50, "FIg." should be --FIG.--.

Col. 8, line 6, "33" should be --38--.

Signed and Sealed this sixteenth Day of August 1977

[SEAL]

Attest:

RUTH C. MASON
Attesting Officer

C. MARSHALL DANN
Commissioner of Patents and Trademarks